United States Patent [19]
Cartmell et al.

[11] Patent Number: 4,617,935
[45] Date of Patent: Oct. 21, 1986

[54] MEDICAL ELECTRODE

[75] Inventors: James V. Cartmell; Michael J. Allaire, both of Dayton; Michael L. Wolf, West Milton, all of Ohio

[73] Assignee: NDM Corporation, Dayton, Ohio

[21] Appl. No.: 710,994

[22] Filed: Mar. 12, 1985

[51] Int. Cl.⁴ ............................................... A61B 5/04
[52] U.S. Cl. .................................................. 128/641
[58] Field of Search ............... 128/639, 640, 641, 643, 128/696, 783, 785, 798

[56] References Cited

U.S. PATENT DOCUMENTS

| | | | |
|---|---|---|---|
| Re. 31,454 | 12/1983 | Hymes | 128/641 |
| 3,590,810 | 7/1971 | Kopecky | 128/640 |
| 3,972,329 | 8/1976 | Kaufman | 128/2.06 E |
| 3,977,392 | 8/1976 | Manley | 128/641 |
| 3,982,529 | 9/1976 | Sato | 128/641 |
| 4,092,985 | 6/1978 | Kaufman | 128/303.13 |
| 4,226,247 | 10/1980 | Hauser et al. | 128/641 |
| 4,274,420 | 6/1981 | Hymes | 128/641 |
| 4,524,775 | 6/1985 | Rasmussen | 128/640 |

Primary Examiner—William E. Kamm
Assistant Examiner—Randy Citrin
Attorney, Agent, or Firm—Roger S. Dybvig

[57] ABSTRACT

An electrolyte gel matrix, which may be a conductive adhesive such as a urethane hydrogel, is located in a cavity formed in a non-conductive tray. The matrix is adapted to engage the skin of a patient and transmit signals between the skin and an electrode conductor supported by the base of the tray for exchanging signals with peripheral equipment. A stiffening platform adhered to the tray extends across the cavity portion aligned with the conductor to minimize motion artifacts associated with the use of the electrode. The electrode is removably attachable to the skin by an adhesive layer on the lower surface of the tray and by a preferably more aggressive adhesive layer on the lower surface of the platform.

25 Claims, 3 Drawing Figures

U.S. Patent Oct. 21, 1986 4,617,935
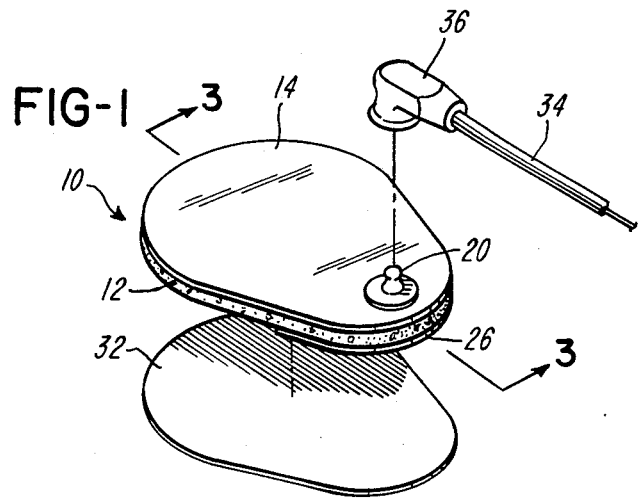
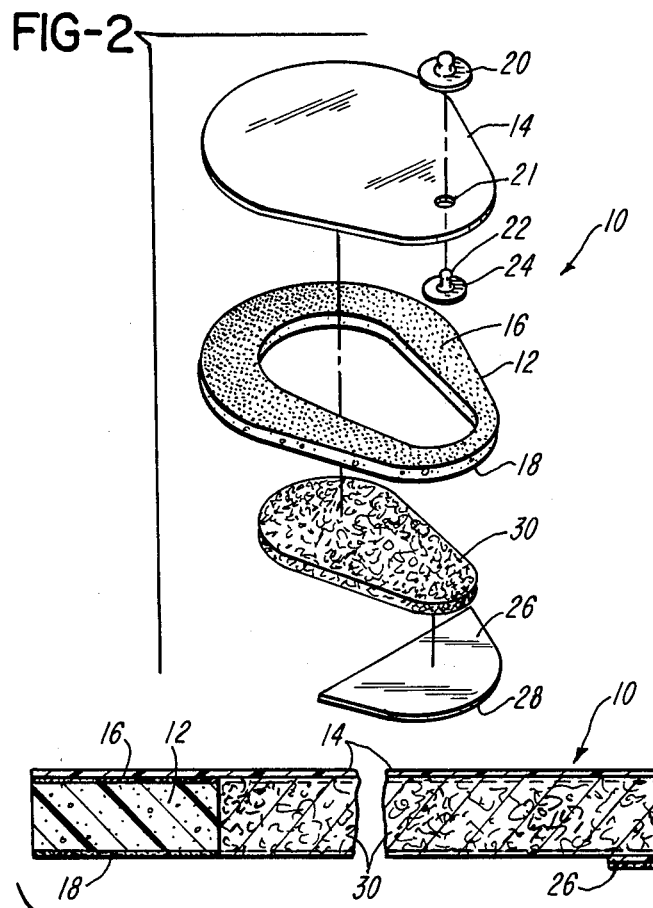

MEDICAL ELECTRODE

SUMMARY OF THE INVENTION

The present invention relates to a medical electrode for transmitting electrical signals between the skin of a subject, such as a medical patient, and peripheral equipment for monitoring signals derived from the skin of the patient. This invention may, however, also be used for medical electrodes for applying stimulation signals to the skin of the patient.

An object of this invention is to provide a medical electrode in which the distortion of signals transmitted by electrode due to motion artifacts is minimized. More particularly, it is an object of this invention to reduce the noise or distortion associated with movements of electrode conductors, such as snap fastener parts, resulting from the tugging or pulling of the electrode conductors by lead wires secured thereto and leading to the peripheral equipment. In many applications, such as in conducting stress test examinations, movements of the patient will cause a relative motion to occur between the lead wire and the electrode conductor so that the electrode conductor is thereby caused to move relative to the skin of the patient producing noise or distortion of the signal derived from the skin.

In accordance with this invention, the electrode comprises an electrically insulating frame having a generally centrally located bore extending completely therethrough that forms a peripheral sidewall or barrier. A first, upper stiffening or cover member overlies and is adhered to the upper surface of the frame. Preferably the outer margins of the cover member are coextensive with the outer margins of the frame and the cover member forms a wall extending completely over the opening in the frame formed by the bore.

The cover member and the frame form a tray having a cavity which is filled by an electrolyte gel matrix that engages and covers the snap fastener eyelet. The gel matrix preferably comprises a conductive adhesive material and there is an adhesive layer on the lower surface of the frame comprising a patient contacting adhesive which is preferably more aggressive than the conductive adhesive matrix. A second, electrically insulating, stiffening member or platform is adhered to the lower surface of the frame and is adhered to and covers a portion of the gel matrix. Interfitting electrically conductive snap fastener and eyelet members are clenched to the stiffening member in alignment with the portion of the bore covered by the second stiffening member. The second stiffening member also has a patient contacting adhesive layer on its lower surface which preferably comprises a more aggressive adhesive material than the material used for the patient-contacting layer on the lower surface of the frame.

In use, the electrode is applied to the skin of a patient and held thereon by the patient-contacting adhesive on the lower surface of the frame, by the preferably more aggressive adhesive on the lower surface of the second stiffening member or platform, and, in the preferred embodiment, by the conductive adhesive electrolyte gel matrix. Since the area of contact between the patient's skin and the electrolyte gel matrix is not aligned with, but is offset from, the electrode conductor, the second stiffening member or platform constitutes a barrier that shields the gel matrix portion aligned with the electrode conductor from either chemical or physical interaction with the skin of the patient. The second stiffening member or platform also cooperates with the cover member to render the area surrounding the electrode conductor quite stiff. As a result of the foregoing features of the electrode of this invention, movements of the electrode conductor, such as caused by pulling of the lead wire, have a substantially lesser effect upon the purity of the signal transmitted than is the more typical case in which the electrode conductor is centrally located over an electrolyte engaging the skin.

The frame and its bore could have substantially any shape provided that the frame provides a complete wall or barrier surrounding the electrolyte gel matrix. The presently preferred shape of both the frame and its bore are generally elliptic, somewhat in the shape of a horse collar, or more precisely in the form of a triangle having a rounded or radiused base and a rounded or radiused apex so that the cavity enclosed by the frame is relatively larger at one end portion and relatively smaller at its opposite end portion. The snap fastener or other electrode conductor is preferably located in alignment with the smaller end portion of the bore and the second stiffening member or platform is adhered to and covers only the smaller end portion of the frame and the gel matrix. Accordingly, the electrode is quite stiff, almost rigid, in the area immediately around the electrode conductor and, advantageously, a relatively large area of the gel matrix engages the patient's skin.

Other objects and advantages of this invention will become apparent from the following description.

BRIEF DESCRIPTION OF THE DRAWINGS

FIG. 1 is a perspective illustration of the medical electrode of the present invention with a lead wire and release paper exploded away from the medical electrode.

FIG. 2 is an exploded perspective illustration of the medical electrode of FIG. 1.

FIG. 3 is a fragmentary section view taken substantially along the line 3—3 of FIG. 1.

DETAILED DESCRIPTION OF THE PREFERRED EMBODIMENT

Having reference to the drawings, the medical electrode of the present invention is generally identified by the reference number 10 and includes an electrically insulating frame 12, preferably comprising a foam plastic material such as a closed cell polyethylene, assembled upon a first, upper stiffening or cover member 14, which has a shape, when viewed in plan, having the appearance of a falling raindrop. The frame 12 comprises an elliptic body forming a wall or barrier along the entire periphery of the lower face of the cover member 14. For this purpose, the frame is adhered to the cover member 14 by an upper adhesive layer 16 shown formed on the upper surface of the frame 12 but which could be coated on the lower surface of the cover member 14 or, alternatively, could comprise a separate, double-sided adhesive sheet.

It will be noted that the frame 12 somewhat resembles a horse collar in that the area surrounded by the frame 12 is an elongated area which is relatively wide at one end and relatively narrow at its opposite end. More precisely, both the frame 12 and the area it surrounds are in the form of triangles having a rounded or radiused apex and a rounded or radiused base. The outer margins of the cover member 14 and the frame 12 are preferably mutually coextensive and the cove member 14 is perforated centrally within its narrow end to have an aperture 21 aligned generally centrally within the rounded apex of the region bounded by the frame 12. The aperture 21 receives an electrode conductor which, as illustrated, is preferably formed from interfitting snap fastener parts comprising a stud 20, that projects outwardly of the cover member 14, and an eyelet 22. Although having the appearance of a pre-punched hole in FIG. 2, the aperture 21 may be created by piercing when the snap fastener parts are mated with one another to clench the cover member 14. The eyelet 22 has a head 24 which bears against the lower surface of the cover member 14 and seals around the aperture 21.

To facilitate the transmission of signals, it is preferred that the eyelet 22 comprises substantially pure silver or be plated or coated with substantially pure silver and that its head 24 be chlorided. Thus, eyelet 22 could be substantially pure, solid silver or, for example, it could comprise silver plated ABS or a silver painted conductive plastic. Other metals could be used such, for example, as stainless steel, as those familiar with the art will be well aware. The stud 20, since it merely serves as a terminal for connection of the eyelet 22 to peripheral equipment, may be made of any suitable conducting material, such as silver plated brass or stainless steel.

The lower surface of the frame 12 is covered by or adhered to an intermediate adhesive layer 18. The frame 12 forms the base and the cover member 14 forms the sidewall of a tray assembly defining a cavity filled with an electrolyte gel matrix 30 which engages and covers the head 24 of the eyelet 22. The electrolyte gel matrix 30 could comprise a conventional, open cell foam gel pad filled with a suitable electrolyte, but preferably comprises a conductive adhesive comprising a polymeric medium, preferably a urethane hydrogel, which is of a gelatinous consistency and which contains an electrolyte in an amount sufficient to render the polymeric medium electrically conductive. As is apparent, the matrix 30 is intended to engage the skin of a patient and preferably slightly overfills the cavity in the tray assembly to insure good skin contact. The electrolyte comprises an ionizable salt compatible with the metal used to form the electrode conductor portion 22. These are well known in the art; examples are the use of sodium chloride when the snap fastener eyelet 22 is made from or coated with silver and the use of sodium sulfate with stainless steel. The polymeric medium forming the matrix 30 is tailored to have adequate adhesive qualities to adhere to the skin of a patient and adequate cohesive strength so that it substantially maintains its shape. While the foregoing remarks have indicated that a urethane hydrogel is preferred, those skilled in the art will appreciate that numerous other polymeric, conductive adhesive materials may be used to form the matrix 30.

As best appears in FIG. 2, the lower surface of the frame 12 is covered at its smaller end portion by a second, electrically insulating stiffening member or platform 26 which also engages the lower surface, as appears in FIG. 2, of the matrix 30. The platform 26 has an outer margin curved to match the outer margin of the smaller end of the frame 12. The platform 26 is retained in position by means of the confronting parts of the intermediate adhesive layer 18 and, in the preferred embodiment, by the adhesive matrix 30. The lower surface of the platform 26, opposite the adhesive layer 18, is coated by a lower adhesive layer 28. Preferably, the adhesive material of the lower layer 28 is relatively highly aggressive as compared to the adhesive of the intermediate layer 18. Thus the adhesive of the intermediate layer 18 is formulated to allow the upper surface of the frame 12 to be easily peeled from the patient's skin whereas the adhesive of the lower layer 28 is formulated to be more difficult to peel from the skin.

The conductive adhesive of choice for use to form the matrix 30 of the present invention is a urethane hydrogel so formulated as to have a modest tack to skin but to be readily peelable from the skin without leaving any appreciable residue as the electrode is peeled from the skin. The intermediate adhesive layer 18 on the lower surface of the frame 12 is preferably a more aggressive adhesive so that a good seal is formed around the matrix 30 between the frame 12 and the skin. Since the cover member 14 and its associated snap fastener assembly 20, 22 cooperate with the upper adhesive layer 16 on the upper surface of the frame 12 to cover and seal one side of the cavity in the frame 12, and the patient's skin cooperates with the lower adhesive layer 18 to seal the opposite side of the cavity, the electrode 10 when in use is well protected from evaporation or dry-out of the electrolyte gel matrix 30.

A significant problem encountered when using medical electrodes is the development of spurious signals, called "motion artifacts", resulting from relative movements between the snap fastener assembly or other electrode conductor and the skin. It is of course unavoidable that when a lead wire has been connected from the stud 20 to remote equipment, movements by the patient will result in movements of the snap fastener assembly 20, 22 relative to the electrolyte gel matrix 30 and the underlying skin. The effects of such relative movements upon the signal being transmitted with the electrode of this invention are believed to be minimized for the following reasons: (1) the platform 26 cooperates with the cover member 14 to cause the smaller end of the electrode to be quite stiff, thereby to resist movements of the snap fastener assembly 20, 22 relative to the frame 12 and the conductive adhesive matrix 30; (2) movements of the snap fastener assembly relative to the skin are minimized because of the stiffness of the electrode portion around the snap fastener assembly and because such portion is strongly adhered to the skin by the more aggressive adhesive of layer 28 on the bottom of the platform 26; (3) being aligned with the snap fastener assembly 20, 22, the platform 28 provides an insulating barrier between the skin and the conductive adhesive matrix 30 so that the only portion of the conductive adhesive matrix 30 used to transmit signals from the skin to the snap fastener assembly 20, 22 are non-aligned with, or offset from, the snap fastener assembly; and (4) the compliancy of the conductive adhesive matrix 30 further reduces the effects that motions of the assembly 20, 22, as may be caused by pulling or tugging by the lead wire, may have on the quality of the signals transmitted.

In the preferred construction, the cover member 14 and the stiffening platform 26 are fabricated from polyethylene terephthalate having a thickness in the range of approximately 1-5 mils. A thickness of 3 mils is presently preferred since thinner sheets or films do not adequately stiffen the electrode and thicker sheets detract from the ability of the electrode to conform to the body contours with which the electrode is to be used. The frame 12 is preferably formed from a $\frac{1}{8}$th inch thick sheet of polyethylene foam. Other foam plastics, such as polyvinyl chloride, may also be used. The intermediate and lower skin-contacting adhesive layers 18 and 28 may comprise conventional medical grade pressure sensitive adhesives. The upper adhesive layer 16 may be any adhesive suitable for its purpose.

The medical electrode 10 is protected during shipment and storage by a release liner 32 which lies under the electrode as illustrated in FIG. 1 and is thus lightly adhered to the lower adhesive layer 18 and also the adhesive layer 28.

In preparation for use of the electrode 10 on a patient, the release liner 32 is removed from the electrode and the electrode mounted to the skin of the patient by means of the adhesive layers 18 and 28. The electrode is then connected electrically to remote equipment for monitoring or issuing stimulation signals by means of a lead wire 34 having an appropriate snap fastener connector received in an insulating housing 36. Upon completion of the monitoring or stimulation procedure, the electrode 10 may be peeled from the skin of the patient by first peeling the end of the annular frame 12 which is remote from the stiffening platform 26 away from the patient's skin, then pulling the stiffening platform 26 from the patient's skin by the exertion of a force greater than was initially required for the peeling procedure.

Although the presently preferred embodiment of this invention has been described, it will be understood that various changes may be made within the scope of the appended claims.

Having thus described our invention, we claim:

1. A medical electrode comprising:
    electrically insulating means forming a tray having a cavity, said tray forming means comprising a cover member forming the base of said tray, and a frame connected to said cover member and forming a sidewall around said cavity;
    conductor means supported by said cover member having one portion located within one portion of said tray and another portion projecting outwardly of said cover member for transmitting signals between the skin of a patient and peripheral equipment, said conductor means extending only into said one portion of said tray and not into the remainder of said tray; an electrolyte gel matrix filling said cavity and having one portion engaging and covering said one portion of said conductor;
    electrically insulating platform means connected to said frame and spanning across a first part of said gel matrix including said one portion of said electrolyte gel matrix covering said conductor means for providing a barrier that covers and thereby shields said one portion of said gel matrix from either chemical or physical interaction with the skin of a patient to which the electrode may be applied, said first part of said gel matrix comprising less than the entire said matrix, and said gel matrix having a second part exposed by said tray and said platform means for engagement with the skin of a patient; and
    adhesive means for adhering said platform means and said frame to the skin of a patient with said second part of said electrolyte gel matrix engaging the skin.

2. The medical electrode of claim 1 wherein said one portion of said conductor means comprises a substantially pure silver, a portion of which engaging said matrix has been chlorided.

3. The medical electrode of claim 2 wherein said one portion of said conductor means comprises a snap fastener eyelet and said another portion comprises a snap fastener stud.

4. The medical electrode of claim 1 wherein said frame is so shaped that the cavity surrounded by said frame has a wider end and a narrower end when viewed in plan.

5. The medical electrode of claim 4 wherein said one portion of said conductor means extends only into said narrower end of said cavity.

6. The medical electrode of claim 4 wherein said cover member comprises a relatively flat plastic sheet, and wherein said cover member and said frame have mutually coextensive peripheral shapes.

7. The medical electrode of claim 1 wherein said frame is adhesively secured to said cover member.

8. The medical electrode of claim 1 wherein said adhesive means comprises a pressure sensitive adhesive on the lower surface of said frame and further comprises a pressure sensitive adhesive on the lower surface of said platform means which is more aggressive than said adhesive on the lower surface of said frame.

9. The medical electrode of claim 1 wherein said cover member comprises a first stiffening sheet, said frame comprises a foamed plastic sheet secured adhesively to said first stiffening sheet, and said platform comprises a second stiffening sheet.

10. The medical electrode of claim 9 wherein said cover member and said platform means comprise polyethylene terephthalate sheet members and wherein said frame comprises a polyethylene foam.

11. The medical electrode of claim 10 wherein said polyethylene terephthalate sheet members have a thickness in the range of one to five mils.

12. The medical electrode of claim 1 wherein said electrolyte gel matrix comprises a conductive adhesive.

13. The medical electrode of claim 12 wherein said conductive adhesive comprises a polymeric material.

14. A medical electrode comprising:
    electrically insulating means forming a tray having a cavity, said tray forming means comprising a cover member forming the base of said tray, and a frame connected to said cover member and forming a sidewall around said cavity;
    conductor means supported by said cover member having one portion located within one portion of said tray and another portion projecting outwardly of said cover member for transmitting signals between the skin of a patient and peripheral equipment, said conductor means extending only into said one portion of said tray and not into the remainder of said tray;
    an electrolyte gel matrix filling said cavity and having one portion engaging and covering said one portion of said conductor, said gel matrix comprising a polymeric medium which contains an electrolyte in an amount sufficient to render the polymeric medium electrically conductive;
    electrically insulating platform means connected to said frame and spanning across a first part of said gel matrix including said one portion of said electrolyte gel matrix covering said conductor means for providing a barrier that covers and thereby shields said one portion of said gel matrix from either chemical or physical interaction with the skin of a patient to which the electrode may be applied, said first part of said gel matrix comprising less than the entire matrix, and said gel matrix having a second part exposed by said tray and said platform means for engagement with the skin of a patient; and adhesive means for adhering said platform means and said frame to the skin of a patient with said second portion of said electrolyte gel matrix engaging the skin.

15. The electrode of claim 14 wherein said polymeric medium comprises a urethane hydrogel.

16. The medical electrode of claim 15 wherein said one portion of said conductor means comprises a substantially pure silver, a portion of which engaging said matrix has been chlorided.

17. The medical electrode of claim 16 wherein said one portion of said conductor means comprises a snap fastener eyelet and said another portion comprises a snap fastener stud.

18. The medical electrode of claim 15 wherein said frame is so shaped that the cavity surrounded by said frame has a wider end and a narrower end when viewed in plan.

19. The medical electrode of claim 18 wherein said one portion of said conductor means extends only into said narrower end of said cavity.

20. The medical electrode of claim 18 wherein said cover member comprises a relatively flat plastic sheet, and wherein said cover member and said frame have mutually coextensive peripheral shapes.

21. The medical electrode of claim 15 wherein said frame is adhesively secured to said cover member.

22. The medical electrode of claim 15 wherein said adhesive means comprises a pressure sensitive adhesive on the lower surface of said frame and further comprises a pressure sensitive adhesive on the lower surface of said platform means which is more aggressive than said adhesive on the lower surface of said frame.

23. The medical electrode of claim 15 wherein said cover member comprises a first stiffening sheet, said frame comprises a foamed plastic sheet secured adhesively to said first stiffening sheet, and said platform comprises a second stiffening sheet.

24. The medical electrode of claim 23 wherein said cover member and said platform means comprise polyethylene terephthalate sheet members and wherein said frame comprises a polyethylene foam.

25. The medical electrode of claim 24 wherein said polyethylene terephthalate sheet members have a thickness in the range of one to five mils.

* * * * *